US010598636B2

(12) United States Patent
Davis et al.

(10) Patent No.: US 10,598,636 B2
(45) Date of Patent: Mar. 24, 2020

(54) ULTRASONIC WELD ANALYSIS FOR ORTHOTROPIC STEEL DECKING SYSTEMS IN BRIDGES

(71) Applicant: VeriPhase, Inc., Birmingham, AL (US)

(72) Inventors: John Mark Davis, Hoover, AL (US); Archibald Leach Cobbs, Mountain Brook, AL (US); Charles Allan Hansen, Sterrett, AL (US); Nicholas James Bublitz, Chelsea, AL (US); Samuel Matthew Davis, Birmingham, AL (US)

(73) Assignee: VeriPhase, Inc., Birgmingham, AL (US)

( * ) Notice: Subject to any disclaimer, the term of this patent is extended or adjusted under 35 U.S.C. 154(b) by 0 days.

(21) Appl. No.: 16/375,611

(22) Filed: Apr. 4, 2019

(65) Prior Publication Data
US 2019/0234912 A1    Aug. 1, 2019

Related U.S. Application Data

(63) Continuation-in-part of application No. 14/986,195, filed on Dec. 31, 2015, now Pat. No. 10,324,066, and
(Continued)

(51) Int. Cl.
*G01N 29/48*  (2006.01)
*G01N 29/265* (2006.01)
*G01N 29/22*  (2006.01)

(52) U.S. Cl.
CPC ........... *G01N 29/48* (2013.01); *G01N 29/265* (2013.01); *G01N 29/221* (2013.01);
(Continued)

(58) Field of Classification Search
CPC .... G01N 29/48; G01N 29/265; G01N 29/221; G01N 2291/02854; G01N 2291/056; G01N 2291/2675
See application file for complete search history.

(56) References Cited

U.S. PATENT DOCUMENTS

2004/0011773 A1*  1/2004  Fritz .................... B23K 26/03
                                                         219/121.83
2005/0132809 A1   6/2005  Fleming et al.
(Continued)

OTHER PUBLICATIONS

Venkatraman et al. "Thermography for Online Detection of Incomplete Penetration and Penetration Depth Estimation." In:12th A-PCNDT 2006-Asia-Pacific Conference on NDT.
(Continued)

*Primary Examiner* — Natalie Huls
(74) *Attorney, Agent, or Firm* — The Gache Law Firm, P.C.; Russell C. Gache

(57) ABSTRACT

A system provides for the calculation of the penetration depth of a weld in an orthotropic steel decking system. Weld scan section data is accessed and each scan section along the weld seam is processed to find the amount of penetration as a percentage of the thickness of the rib leg metal at the weld location. The amount of penetration is calculated by finding ultrasonic reflections recorded as voxels that have the greatest magnitude within an area of contiguous magnitudes and then determining the location of those voxels relative to the weld geometry and distance along the thickness of the rib leg steel. A report for each section scan and the entire weld seam may be generated for review by a weld inspector that allows for spot inspections of specified areas along the weld seam for possible weld remediation.

20 Claims, 6 Drawing Sheets

Related U.S. Application Data a continuation-in-part of application No. 15/866,571, filed on Jan. 10, 2018, now Pat. No. 10,551,351.

(52) U.S. Cl.
CPC ............. *G01N 2291/02854* (2013.01); *G01N 2291/056* (2013.01); *G01N 2291/2675* (2013.01)

(56) References Cited

U.S. PATENT DOCUMENTS

| | | |
|---|---|---|
| 2007/0038400 A1 | 2/2007 | Lee et al. |
| 2007/0253519 A1* | 11/2007 | Meier ................ G01N 29/2487 376/260 |
| 2008/0072674 A1* | 3/2008 | Ume ................. G01N 29/0618 73/627 |
| 2009/0320598 A1* | 12/2009 | Puchner ............... G01N 29/075 73/588 |
| 2010/0064495 A1 | 3/2010 | Iizuka et al. |
| 2010/0123080 A1* | 5/2010 | Andres ................ B23K 9/0956 250/341.6 |
| 2011/0083512 A1 | 4/2011 | Imbert et al. |
| 2011/0183304 A1 | 7/2011 | Wallace et al. |
| 2016/0139593 A1* | 5/2016 | Willett ................ B23K 26/032 700/109 |
| 2016/0231291 A1 | 8/2016 | Boulware et al. |
| 2018/0056447 A1* | 3/2018 | Todorov ............... B23K 31/125 |
| 2018/0136169 A1* | 5/2018 | Ume ..................... G01N 29/04 |

OTHER PUBLICATIONS

Qian et al. "Fatigue Failure of Welded Connections at Orthotropic Bridges." In: Frattura ed 1-20 Integrit, Strutturale 9(9) Jul. 2009, [online] [retrieved on Jun. 6, 2019].

\* cited by examiner

| | A | D | E | F | P | Q | R | S | T |
|---|---|---|---|---|---|---|---|---|---|
| 1 | Num | Scan Position | Main Angle | Main Amp% | Height U(m-r) | Input T Pen % | Median T Pen % | Accept/ Reject | Evaluator Notes |
| 2 | 1 | 0.000 | | | | | | | Drop-out detected |
| 3 | 2 | 0.039 | | | | | | | Loss of couplant detected |
| 4 | 3 | 0.078 | | | | | | | Review recommended |
| 5 | 4 | 0.118 | | | | | | | Review recommended |
| 6 | 5 | 0.157 | | | | | | | Review recommended |
| 24 | 23 | 0.866 | 60.25 | 21.6 | 0.036 | 91 | 91 | | |
| 25 | 24 | 0.905 | 60.50 | 14.9 | 0.043 | 89 | 89 | | |
| 26 | 25 | 0.944 | 61.00 | 16.5 | 0.039 | 90 | 90 | | |
| 27 | 26 | 0.984 | 61.50 | 19.6 | 0.034 | 91 | 91 | | |
| 28 | 27 | 1.023 | 61.25 | 23.9 | 0.007 | 98 | 98 | | |
| 29 | 28 | 1.062 | 61.25 | 29.4 | 0.010 | 97 | 97 | | |
| 30 | 29 | 1.102 | 61.00 | 20.8 | 0.014 | 96 | 96 | | |
| 31 | 30 | 1.141 | 61.00 | 14.9 | 0.014 | 96 | 96 | | |
| 35 | 34 | 1.299 | 60.75 | 14.1 | 0.038 | 90 | 90 | | |
| 36 | 35 | 1.338 | 60.75 | 19.6 | 0.038 | 90 | 90 | | |
| 37 | 36 | 1.377 | 60.75 | 17.6 | 0.035 | 91 | 91 | | |
| 38 | 37 | 1.417 | | | | | | | Review recommended |
| 39 | 38 | 1.456 | | | | | | | Review recommended |
| 40 | 39 | 1.495 | | | | | | | Review recommended |
| 41 | 40 | 1.535 | 60.25 | 22.4 | 0.028 | 93 | 93 | | |
| 42 | 41 | 1.574 | 60.50 | 28.2 | 0.024 | 94 | 94 | | |
| 607 | 606 | 23.815 | 59.50 | 27.8 | 0.075 | 81 | 81 | | |
| 608 | 607 | 23.854 | 59.50 | 42.4 | 0.074 | 81 | 81 | | |
| 609 | 608 | 23.894 | 59.00 | 12.5 | 0.126 | 67 | 67 | | |
| 610 | 609 | 23.933 | 59.50 | 56.1 | 0.071 | 82 | 82 | | |
| 611 | 610 | 23.972 | 59.50 | 69.0 | 0.074 | 81 | 81 | | |
| 1784 | 1783 | 70.147 | 60.25 | 61.2 | 0.066 | 83 | 83 | | |
| 1785 | 1784 | 70.186 | 60.25 | 71.4 | 0.047 | 88 | 88 | | |
| 1798 | 1797 | 70.698 | 61.00 | 12.5 | 0.103 | 73 | 73 | | |
| 1799 | 1798 | 70.737 | | | | | | | Review recommended |
| 1800 | 1799 | 70.776 | 62.00 | 10.6 | 0.124 | 68 | 68 | | |
| 1801 | 1800 | 70.816 | 59.00 | 12.5 | 0.129 | 67 | 66 | | |
| 1802 | 1801 | 70.855 | 60.75 | 37.3 | 0.052 | 86 | 86 | | |
| 1803 | 1802 | 70.895 | 60.75 | 37.3 | 0.052 | 86 | 86 | | |
| 1804 | 1803 | 70.934 | 60.50 | 26.7 | 0.032 | 92 | 92 | | |
| 1805 | 1804 | 70.973 | 60.00 | 36.1 | 0.030 | 92 | 92 | | |
| 1806 | 1805 | 71.013 | 60.25 | 32.2 | 0.005 | 99 | 99 | | |
| 1807 | 1806 | 71.052 | 59.75 | 16.9 | 0.018 | 95 | 95 | | |
| 1808 | 1807 | 71.091 | 60.25 | 23.9 | 0.026 | 93 | 93 | | |
| 1809 | 1808 | 71.131 | 60.00 | 36.5 | 0.030 | 92 | 92 | | |

Inspection Summary | ScanCheck Report | Gr_2 lop

FIG. 7

ULTRASONIC WELD ANALYSIS FOR ORTHOTROPIC STEEL DECKING SYSTEMS IN BRIDGES

This application claims the benefit of filing priority under 35 U.S.C. § 119 and 37 C.F.R. § 1.78 of the co-pending U.S. non-provisional application Ser. No. 14/986,195 filed Dec. 31, 2015, for a System and Method for the Improved Analysis of Ultrasonic Weld Data. All information disclosed in that prior pending nonprovisional application is hereby incorporated by reference.

FIELD OF THE INVENTION

The present invention relates generally to ultrasonic testing of welds. In particular, the present invention relates the ultrasonic testing of welds for orthotropic decking in bridges.

BACKGROUND OF THE INVENTION

Modern bridges include separate elements coordinated together to create a strong and durable structure designed to last for many decades or longer. One of those bridge elements is a bridge deck, which provides the support for and the surface upon which man and machine may traverse over whatever the bridge is spanning. In a vehicular bridge, the primary function of the bridge deck is to support the vehicular traffic safely on a smooth and reliable surface, but also to receive the vehicular vertical loads and distribute those loads to the steel superstructure of the bridge.

A bridge deck is typically continuous along the span of the bridge and continuous across the width of the span. In most applications, the bridge deck is made of composite materials, with the steel superstructure supporting it through positive attachment to the girders, such as using shear connecters to attach the concrete deck slabs to steel girders. In such cases, the deck serves as part of the top flange in the composite section and is utilized to provide strength and stiffness to the bridge.

A bridge deck is subjected to various 3-dimensional forces, including local flexural bending of the slab spanning over the girders in the transverse direction caused by the vehicle wheel loads, and is subjected to longitudinal stresses caused by flexure along the bridge span. The deck, when positively attached to the girders, provides continuous bracing of the top flange in the finished structure, and provides stability to the overall bridge system. The deck also acts as a horizontal diaphragm that is capable of transferring lateral loads, such as wind or seismic loads, to the supports.

Often, especially in the United States, reinforced concrete deck slabs are used as the deck for steel bridges. Concrete deck slabs can be constructed with cast-in-place or precast methods, and typically include mild steel reinforcement in the longitudinal and transverse directions. Although not common to typical steel bridges, concrete decks can utilize post-tensioning steel in addition to the mild steel reinforcement in an effort to provide additional strength and durability. While well understood and common in bridge building, the use of concrete slabs as a deck presents tremendous weight loads on the primary structures of a bridge, such as the primary cables in a suspension bridge or counter-lever steel beams in a counter levered bridge. The designers of bridges using concrete decks take theses loads into account when they design the construction of the bridge.

An alternative to a concrete deck is an orthogonal-anisotropic deck, or as more commonly known an "ortho-tropic" deck, which is typically made of steel. Orthotropic Steel Decks are referred to in the construction industry as an "OSD" systems and are used in many of the world's modern bridge structures. Use of OSD system does a good job to distribute vehicular traffic loads across the extended deck surface, and provide stiffening of the relatively slender plate elements of an OSD that are under continual compressive and active loading. One well-known example of an OSD based bridge is the recently replaced San Francisco Oakland Bay Bridge which replaced a common concrete slab deck arrangement after an earthquake destroyed a portion of the bridge in the 1980s.

An OSD system consists of a flat, thin steel plate, stiffened by a series of closely spaced longitudinal ribs with support by orthogonal transverse floor beams. The OSD is efficient in that it is integral with the supporting bridge superstructure framing as a top flange common to both the transverse floor beams and longitudinal girders. This results in increased rigidity and material savings in the design of these components. As with other conventional steel-framed construction, loads are generally transferred by the floor beams transversely to the main load carrying system, such as longitudinal girders. This design is far more cost effective than the common use of concrete slabs with steel rebar reinforcing. Instead, orthotropic decks are fairly hollow on the inside and make bridge decks lighter which reduces the weight requirements of the bridge super structure. However, in additional to reduced weight requirements of the super structure, a defining characteristic of the OSD bridge is that it results in a nearly all steel superstructure which has the potential (with minimal maintenance) to provide extended service life and standardized modular design, as compared to more conventional bridge construction.

As is widely recognized, OSD construction has tremendous potential for use in short to medium span "workhorse" girder bridges when located on a high-volume roadway where accelerated construction or extended service life is required. Further, there is a recent trend in the foreign countries, and especially in Asia, towards using bridge systems that are more rapidly constructed to provide traffic solutions that offer long-term durability and economy with the goal of 100 years of service life. Part of the popularity of the OSD bridge is that it can be constructed quickly because most of the components may be prefabricated in high volume. Additionally, complete future re-decking is rendered unnecessary, which minimizes major traffic impacts in the future. In highly populous regions, such as China, the minimization of traffic impact is paramount once a bridge system is put into service. Furthermore, the OSD provides a smooth continuous riding surface durable against deicing salts with minimal joints to prevent leakage and protect the other bridge components.

However, the bridge construction industry recognizes that OSD bridges have not been problem-free historically, and they present unique challenges in terms of design and construction as compared to conventional bridge construction. Fatigue cracking has been observed more frequently in OSD systems resulting from the complicated weld demands combined with stresses that can be more difficult to quantify and, in particular, which were found in early designs which attempted to overly minimize plate thicknesses to reduce weight. In addition, design loading is determined by live loading (moving vehicles) versus dead loading of the span which requires a precise loading design strategy, and such cyclic live loading dominates the design because fatigue will be the controlling limit for a particular bridge design. Hence, fatigue avoidance in OSD systems requires careful consideration as these systems.

Early analytical tools were limited in their ability to quantify the stress states in these details and the early experimental fatigue resistance database was limited. Moreover, the fatigue performance of many of these details can be sensitive to fabrication techniques. Design and detailing practices relied heavily on experience gained through trial and error. Unfortunately, many trials were unsuccessful, and reports of cracking have occurred in re-decking projects where the interactions between new OSD and existing concrete structure were difficult to account for, and created questions among users especially in the United States as to the long-term effectiveness of OSD systems in the highway infrastructure.

The potential for cracking at the rib-to-deck plate weld is indicative of this problem. Whereas this one-sided weld was once a source of performance issues, it is now executed with a vast increase in consistency and performance by using a partial joint penetration paradigm controlled penetration percentages, and with no tolerance for melt-thru in the welds. Cracking is also possible at the rib-to-floor beam intersections, where 3-dimensional stresses are generated by the in-plane flexure of the floor beam response combined with the out-of-plane twisting from the rib rotations. All of these details have been the subject of extensive research efforts over recent decades, providing better understanding of performance and proper design of OSD systems.

In response to these stress issues, the construction and fabrication techniques employed are very important to the successful use of orthotropic steel bridge decks. Orthotropic steel decks typically require detailed construction specifications and special quality control procedures during fabrication. Current designs typically are not standardized, and thus repetition does not currently help to improve construction and fabrication techniques, however many welding strategies with respect to rib to deck connection and other OSD elements have been refined over the years to ensure the proper distribution of stress across and to and from the decking.

During constructions of an OSD bridge deck, deck plating meeting various ASTM codes are cut to size in accordance with size and design of the bridge and are joined together using either an open or a closed set of steel ribs. The open type of rib arrangement consists of ribs usually made from flat bars, bulb shapes, inverted tee-sections, or angled plate sections. In the closed rib arrangement, the ribs are typically formed into trapezoidal, U-shaped, or V-shaped sections.

The closed-rib system is the preferred system relative to open-ribs for a number of reasons. First, it has much higher flexural and torsional rigidity. The high torsional rigidity contributes to better distribution of concentrated transverse loads and, consequently, to a reduction in stresses in the deck plating. Fewer welds, less distortion, and reduced steel weight are further advantages. However, a complication of the closed rib system is in the execution of the one side partial penetration weld for the rib connection to the deck plate. Various stress and fatigue testing of OSD systems over the years has necessitated the use of a partial penetration weld on the outside of the closed-rib where it attaches to the deck plate (see FIG. 1). This fatigue sensitive weld requires care for fabricators to execute with consistent quality. Also, due to its geometry and inherent torsional strength, closed rib decks are subject to local secondary deformations and stresses that make them vulnerable to fatigue at the intersection at the rib to deck. Furthermore, field splices of the ribs are also more complicated, and this system requires tolerance control in fabrication and erection to ensure proper fit at the splices.

In either case, open or closed, ribs are arranged parallel to the vehicle traffic direction and positioned orthogonally with respect to transverse floor beams, and due to manufacturing costs, trapezoidal shaped rib sections are the most common type of rib shape specified in closed OSD systems because they are more easily pre-fabricated in repeatable sections and they may be lifted into place as a section when completed.

As indicated above, ribs are welded to deck plating using a partial penetration technique. Generally, partial penetration welds are avoided in bridge design and construction because, depending on the joint configuration, associated stiffness, and the applied stress, such welds can be a fatigue concern. In fact, use of the partial penetration weld in the rib to decking is an exception to general AWS provisions to weld several types of joints that will be subjected to tension in the root of the weld. This is why the penetration, melt-through, and root gap must be carefully controlled during weld production in the rib to deck joining. Further, over years of observation and laboratory testing, welds joining rib legs to the underside of the decking plating are the most common area prone to fatigue cracking due to plate deformation, which is caused by the active loading of vehicles moving over the deck surface. Hence, strict quality controls over the partial penetration welds in bridge OSD systems is paramount to bridge construction success.

In melt-though, a small amount of weld material oozes into the backside of the weld joint during the welding process. With blow-through, the weld material spatters through the weld joint. Both of these conditions create sites of potential crack initiation and scrutinized during weld examination, especially blow-through which can be avoided with proper welding technique. It is known that a moderate amount of melt-through is permissible. See FIG. 3. The issued in particular is that the "weld throat" or distance from the "weld face" to the "weld root" must be long enough to ensure a sufficiently strong bond between the deck plate and the rib leg. In addition, testing and experience has shown that a penetration amount of less than 70% provides insufficient weld strength, but a weld penetration amount of greater than 80%, and especially 100%, may lead to fatigue cracking initiated from the weld root when exposed to out-of-plane bending moments. Hence, because bridge plate decking is exposed to continuous cyclic loading from vehicle traffic, it is critical that all partial penetration welds connecting the plate decking to the closed support ribs achieve a minimum of 70% penetration, but not over 80% penetration.

Rib to deck welding should be monitored during any bridge construction project, and ultrasonic penetration testing should be conducted throughout the fabrication process for each portion of the decking constructed to ensure weld penetration compliance. However, ultrasonic testing is time consuming and conducting more testing than is necessary causes unnecessary delays and cost. Additionally, while ultrasonic testing is useful for detecting weld defects and various systems are available for such testing, detecting the penetration of a weld using current ultrasonic testing systems is difficult and not optimized to detect the penetration percentage of welds in a rib to deck weld scenario. In particular, conventional ultrasonic systems (i.e. non-phased array systems) do not have the beam control and resolution to accurately measure the amount of penetration in a weld. First, probes in conventional ultrasonic systems only offer fixed angles of beam profile, and the beam cannot be focused in a real-time analysis. So, penetration height cannot be accurately determined in many instances. Second, conventional ultrasonic systems do not allow a user to focus the beam to provide the necessary resolution to discern certain weld anatomy elements that are required to calculate the penetration of the weld.

In addition, even with phased array ultrasonic systems the time required to do a manual examination of a weld seam along a rib would be impractical. For example, to manually examine a 10-inch weld seam to determine the level of penetration a coarse analysis could be done at 1-inch increments. Data slices or sections would be sized, including the angle to determine height, by moving a beam focusing cursor through the weld at that single scan position, or a 6 db drop (to remove non-substantive noise and defects), and other techniques to determine the penetration. However, each such manual examination would, if performed by a skilled operator would take 20-30 seconds for each slice. So, 10 slices in a 10" weld would take 200-300 seconds or 3 to 5 minutes. However, an accurate determination of a weld seam in order to determine whether the weld seam passes a particular building code specification, such as what is the average penetration depth over a specified distance, requires taking many more samples. A typical sample interval to achieve the data necessary to make a code compliance determination is 0.039 inches separating each sampling slice or section. Expanding on the above estimate, a manual analysis of a 10-inch weld seam using this sampling resolution would require 12.5 hours to 20.8 hours to complete. Extrapolating further, assuming that a road has 4 lanes with 4 ribs per lane (i.e. 8 seams per lane), and the bridge is 1 mile long, the resulting weld seams requiring a single manual inspector would take 9-15 years, working 24 hours a day in a perfect labor and contracting situation. Hence, even for a relatively short bridge of 1 mile, a manual inspection of weld penetrations on such a bridge even if the number of inspectors was increased would be impractical to the point of never being accomplished in any economically viable manner. The result is that only imprecise sampling using manual testing is currently done on OSD systems which leaves bridges with mostly untested rib to deck weld seams, the integrity of which is the most fatigue prone element in any bridge construction project.

Therefore, what is needed is a practical testing system, such as using a phased array testing system, that can quickly and accurately indicate the penetration of a weld in an OSD rib to deck joint.

SUMMARY OF THE INVENTION

It is the object of the present invention to provide a system and method for calculating the penetration depth of a weld in an orthotropic steel decking system. In particular, the present invention provides a method for accessing scan section data for a weld seam for a rib welded to and supporting a steel deck plate. The data is accessed and each scan section along the weld seam is processed to find the amount of penetration as a percentage of the thickness of the rib leg metal at the weld location. The amount of penetration is calculated by finding ultrasonic reflections recorded as voxels that have the greatest magnitude within an area of contiguous magnitudes and then determining the location of those voxels relative to the weld geometry and distance along the thickness of the leg steel. A report for each section scan and the entire weld seam may be generated for review by a weld inspector that allows for spot inspections of specified areas along the weld seam for possible weld remediation.

Other features and objects and advantages of the present invention will become apparent from a reading of the following description as well as a study of the appended drawings.

BRIEF DESCRIPTION OF THE DRAWINGS

A testing system incorporating the features of the invention is depicted in the attached drawings which form a portion of the disclosure and wherein.

DESCRIPTION OF THE PREFERRED EMBODIMENTS

Figure 1:
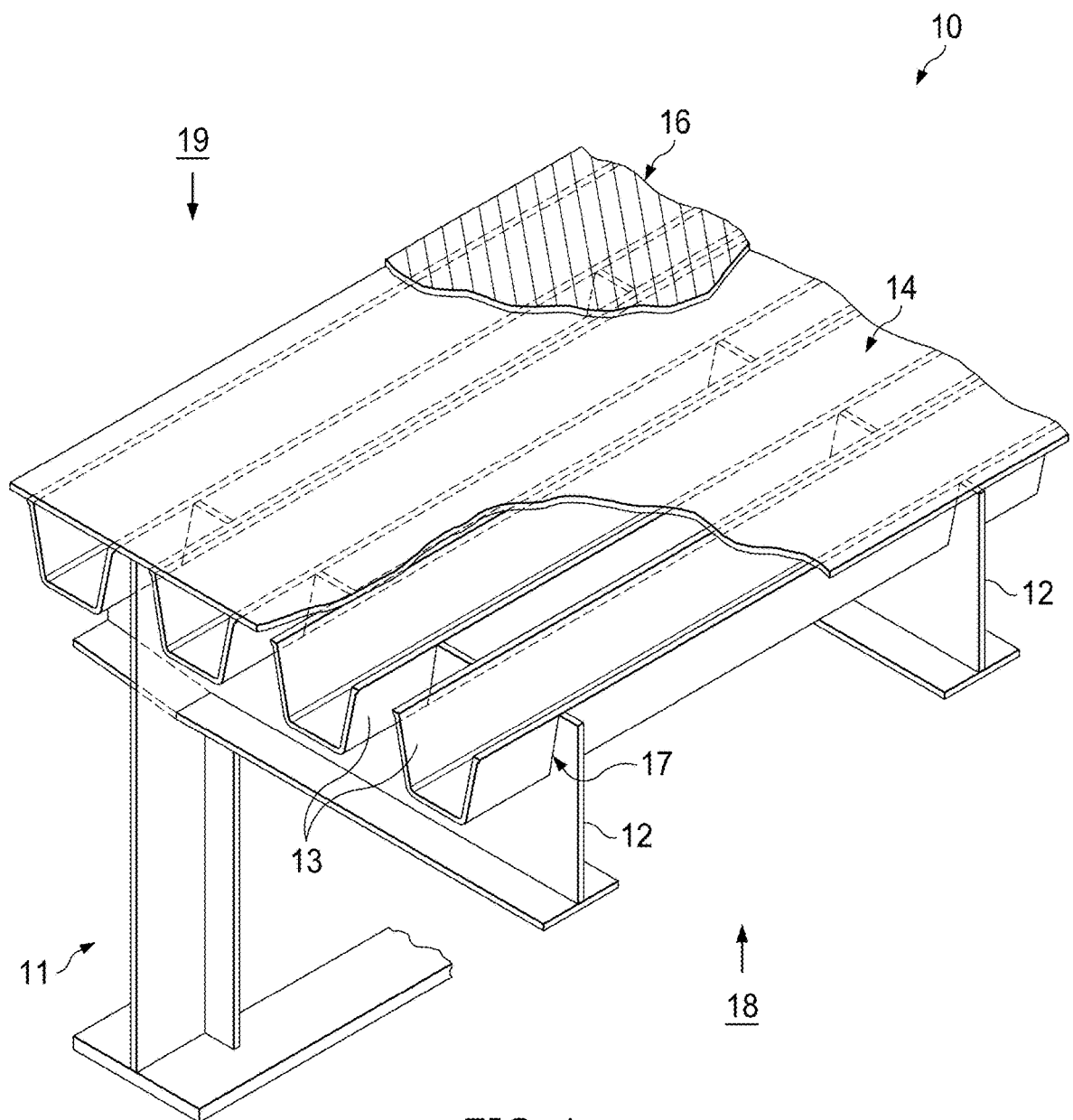
FIG. 1 a perspective view on a portion of bridge decking used in a typical OSD bridge construction project.

Referring to the drawings for a better understanding of the function and structure of the invention, FIG. 1 shows a typical OSD bridge deck section 10 having a supporting bridge super structure, such as a longitudinal plate girder assembly 11, a series of deck floor beams 12 supporting a series of orthogonally positioned trapezoidal shaped ribs 13 spaced from one another and supporting a plurality of steel deck plating 14. A road surface 16 is supported by the deck plating 14 to form a highway for vehicular traffic above the road surface 19, and the super structure 11 supports the highway from below 18. As may be seen, each rib 13 is seated and welded into a notch 17 sized to accept the lower surface of each rib 13, and each rib has two upstanding legs supporting deck plating 14.

Figure 2:
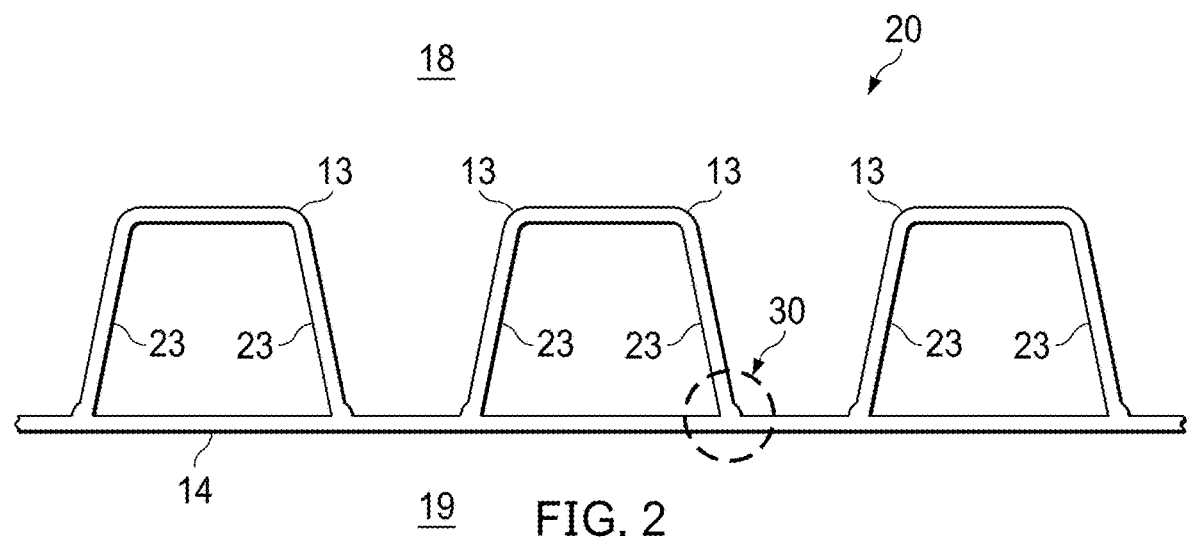
FIG. 2 is an inverted, side elevational view of a series of closed cell ribs welded to deck plating.

In addition to each rib leg 23 supporting deck plating 14, each leg is welded to the deck plating at the contact point as shown in FIG. 2 (inverted from FIG. 1 orientation to better represent actual construction conditions). Each rib 13 is positioned parallel to one another, spaced from one another by a fixed distance, and aligned longitudinally with respect to the flow of vehicular traffic on the roadbed surface 16. Detail 30 shows a sectional view of a weld seam forming the juncture between each leg 23 and the deck plating 14 it is supporting.

Figure 3:
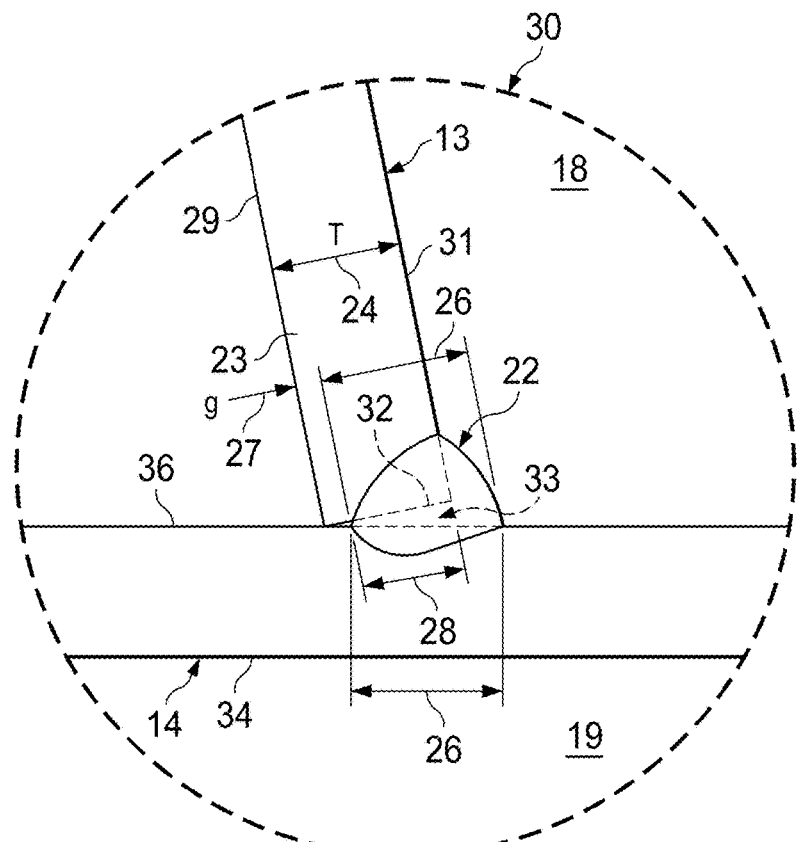
FIG. 3 is a magnified view of the detail indicated in FIG. 2.

Referring now to FIG. 3, a weld section 30 may be seen. Rib leg 23 is positioned against the surface 36 of deck plate 14 and welded to it 22. Rib leg 23 has a width or thickness t 24 and may have its lower edge 32 beveled to contact upper surface 36 flush, or may have a 90-degree angled face thereby forming a slight face gap 33 against surface 36 as shown. The leg portion 23 of rib 13 has an inside or closed side surface 29 and outside or open side surface 31, and deck plate 14 has a topside surface 34 positioned on the upper side or above area 19 of the road surface 16 of the bridge.

As is known in the industry, weld 22 includes a throat width 26 that penetrates into rib leg 23 by a depth 28 d represented by a percentage of rib leg thickness t 24. That percentage is calculated by taking the thickness t 24 and subtracting penetration distance 28, and then calculating that value over the thickness value t 24 as a percentage p. For example, if the thickness t of leg 23 is 0.39 inches and the depth of penetration 28 of weld 22 is 0.312 inches, then the penetration would be calculated by the equation:

$$\left(1 - \frac{t-d}{t}\right) \times 100\% = p$$

Using the example numbers above, penetration p may be calculated as:

$$\left(1 - \frac{.39 - .312}{.39}\right) \times 100\% = 80\%$$

As is known, weld throat distance 26 should be at least as thick as rib width t 24, leaving a gap g 27 that correlates to an open percentage of penetration p and may be calculated with equation:

$$p = \left(1 - \frac{g}{t}\right) \times 100$$

Gap g is obviously going to vary depending upon the penetration amount 28 of the weld 22, and can be a little as zero. Any penetration p greater than 100 percent would constitute a melt through condition. A penetration p of zero would constitute no weld penetration.

Figure 4:
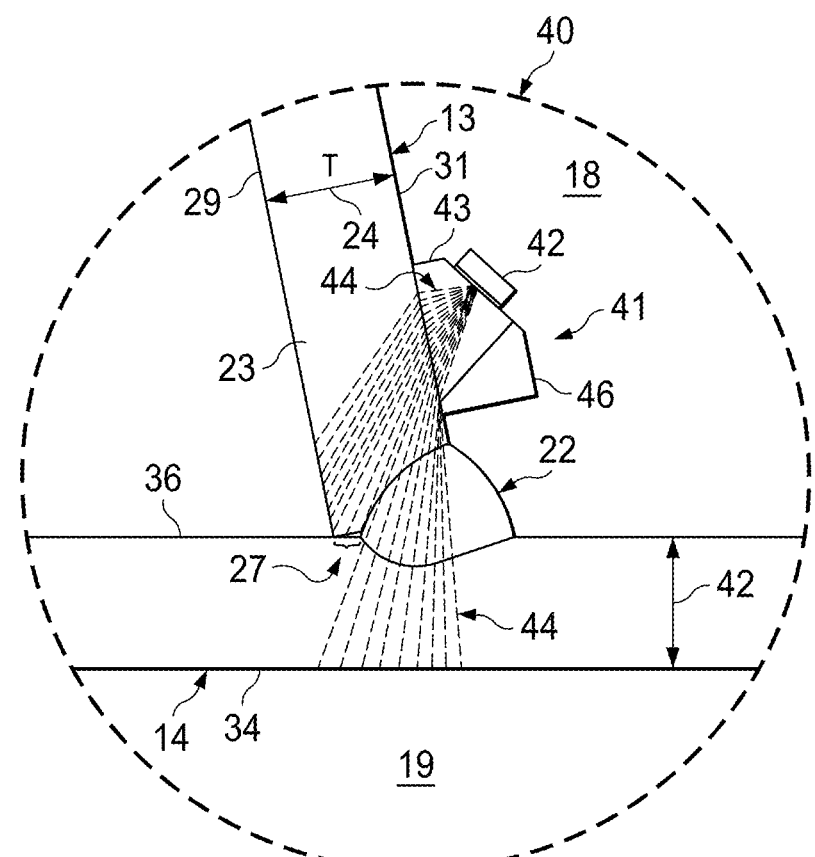
FIG. 4 a detail view of the weld depicted in FIG. 3 and having a phased array ultrasonic probe positioned to test the weld for penetration depth.

Referring now to FIG. 4, a phased array (PA) ultrasonic system probe 41 has been positioned to test weld 22 to measure the weld penetration p for a single data slice or section of a weld seam extending along a continuous lower edge 32 contact point of rib 23 to the undersurface 36 of deck plate 14. Probe 41 includes an ultrasonic transceiver 42 that emits an ultrasonic wave beam 44. A faceted probe block 43 is formed to maintain an predetermined incidence angle to a flat surface optimized for beam conduction into a solid surface positioned underneath the block 43 that is to be analyzed. Bloc 43 includes a dampening portion t 46 that assists in ultrasonic transception on a surface as is known.

When configured for testing, probe 41 is positioned above weld 22 with beam 44 angled downward toward weld as shown. It will be understood that most examinations of weld seams in a rib to deck configuration will be done in a factory situation where the deck plating will be positioned on a supporting work surface with the ribs oriented above the plating. FIG. 4 depicts that typical testing environment, even though later after the deck section 10 has been tested it is inverted again and positioned into place on the bridge superstructure 10 to form an integrated portion of the bridge. With probe 41 in place on outer surface 31 of rib 13 beam, 44 saturates the lower portion of leg 23 and through its lower edge 32 and weld 22. As shown, beam 44 propagates downward against leg inner surface 29, through the weld, and the deck plating 14 provides reflections back to probe 41 for capture by transceiver 42. The probe 41 is moved along seam taking sectional scans at predetermined travel lengths as it moves, and saving each sectional scan in a memory of the PA system for later analysis. A suitable procedure for taking scans, recording those scans, and then analyzing the scans based on voxel amplitudes may be found in U.S. patent application Ser. No. 14/986,195, pages 7-22, and all referenced figures, all of which are hereby incorporated by reference. In association with standard ultrasonic weld analysis techniques, and using the procedure disclosed in the above referenced application for determining voxel reflection amplitude, each voxel angle and range from the emitter 42, gap 27 may be determined, and a percentage of penetration for each scan section for a weld 22 may be found, as will be further explained. It will also be understood per that referenced application that a PAUT (Phased Array Ultrasonic Testing) system such as offered by Olympus Scientific Solutions Americas Inc., based in Waltham, Mass., under the product name OmniScan/OmniPC would be used to view ultrasonic data captured for the weld seam. Further discussion regarding the use of a PAUT system, understanding the testing procedures for welds using such a system, the reading of a PAUT display, the reading of a display produced by an associated PC application to view testing data, and how to calculate the distances and dimensions provided by such a testing application shall not be provided as such information is well understood and not necessary for a complete and full understanding of the herein described invention.

Figure 5:
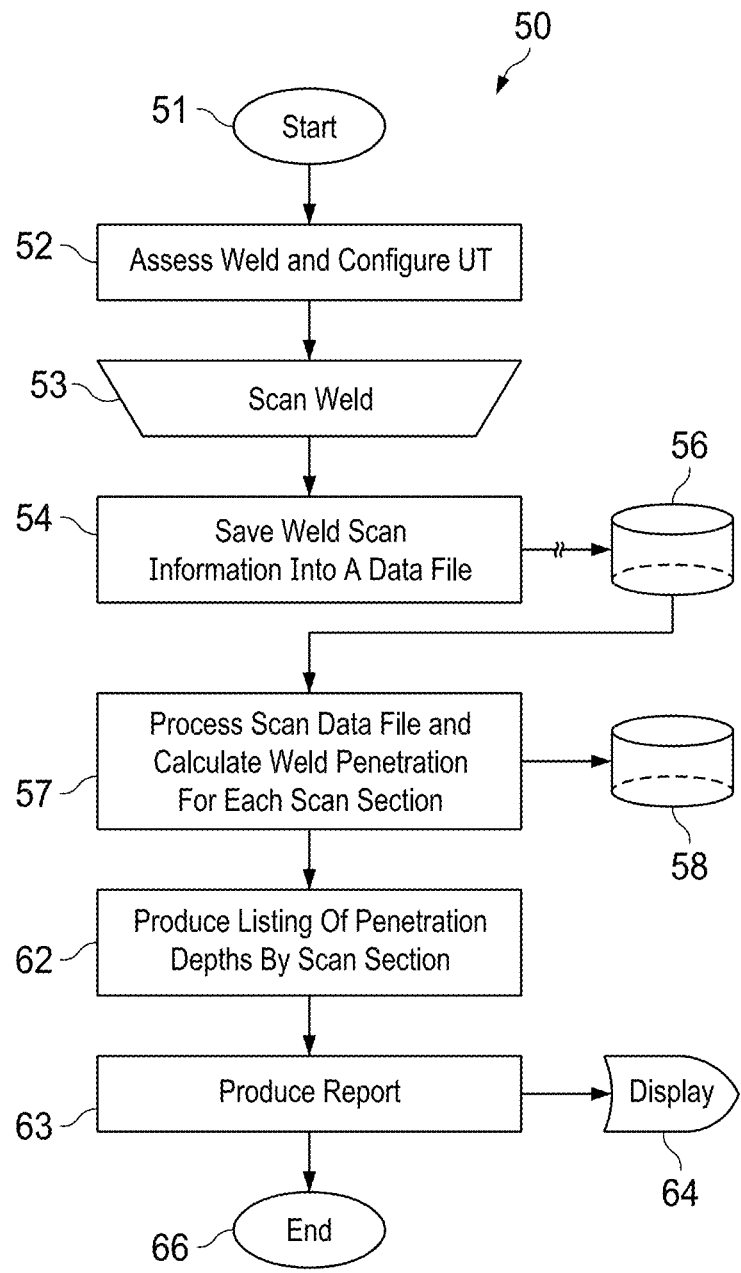
FIG. 5 is a block diagram showing the general steps required to identify the penetration depth of a target weld using the invention.
Figure 6:
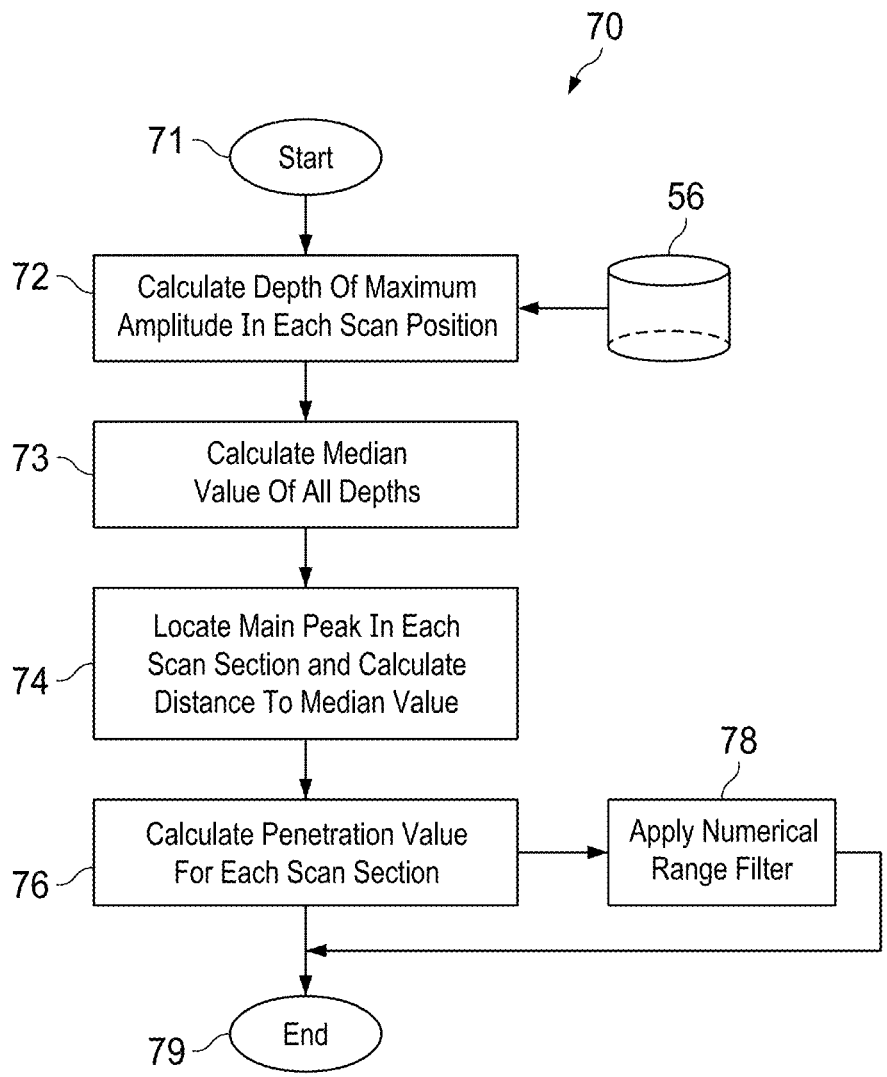
FIG. 6 is a further block diagram showing detailed steps as to how to calculate a penetration value; and, FIG. 7 is a typical report generated from the operation of the claimed invention.

Referring now to FIGS. 5-6, with reference to elements in FIG. 4, a process 50 may be seen for determining the amount of penetration that a continuous weld seam exhibits on average for a determined length and at each sectional scan location. Initially, a PA ultrasonic system suitable for scanning a weld seam is configured 52 for the type and thickness of metal in a weld joint 30, the angle of the rib leg 23 makes with the surface 36 of plating 14, and the distance of the weld seam that is to be scanned. The probe 41 is then moved along the outer surface 31 of rib leg 23 adjacent to weld 22 along the weld seam to obtain section scans 53. As may be understood, the probe may be moved along manually by an operator, or as is becoming more common a motorized robotic carriage may move the probe along the seam at a precisely controlled rate taking scans at predetermined intervals. The scan of the weld seam is saved in a computer memory storage 56, which may be in the PA system being utilized or may be shunted to a cloud-based storage system in real-time via a wireless network.

Once the scan data file has been established, the data file is processed 57 to calculate the weld penetration percentage for each section scan, as well as the median value of penetration for the seam scanned. Processing step 57 may be done at any time of choosing and, as may be understood, may be processed using processors scaled for need in a cloud-based processing system, such as Google's AWS system, or may be processed on a local machine after the data file is downloaded or transferred to that machine. A listing of scan readings may be produced in a report format 62 (see FIG. 7), and any location along the weld seam that has an unacceptable weld penetration may be tracked and visually inspected for remediation if necessary.

Processing step 57 may be further refined as shown in FIG. 6 per steps 70 for calculating a weld penetration. As will be understood from application Ser. No. 14/986,195, each section scan may be analyzed to find a collection of weld amplitudes by voxel position in the scan and recorded for amplitude analysis. Importantly, collections of voxels having similar amplitudes may be grouped for identification as a recognizable feature in the section of the weld under analysis, and each section scan may include a plurality of these common features. As is understood, these collective of magnitude features will visually be interpreted on a PA scanning application display as a blob of similar color, usually have varying shades on the parameter of the blob feature, with each voxel making up the blob having a known location within the section scan.

In process 70, each section scan saved in memory 56 is reviewed and analyzed to find all blobs having contiguous amplitudes above a configurable minimum ("mainPeakMinAmplitude"). Typically, but in accordance with heuristics based on weld inspector experience, this configurable minimum will be 10% of full screen height (FSH) of a PAUT tester display. More technically, the value is established by calculating a range distribution of all amplitudes and only searching for relevant amplitudes above a selected percentage of the highest values (e.g. 25%), as the case may be. This allows for removal of noise and other non-relevant scanning artifacts while being low enough to not exclude any relevant amplitudes. This results in usually one or more blobs in a visual display of the section, but for the purposes of processing they are defined as a grouping of voxels that are present within a defined area with an amplitude signature of substantive value and that are contiguous by location within the scan slice. Contiguous is defined as, assuming the requisite amplitude, two voxels being adjacent to one another where adjacent is further defined as the two voxels differing in location by at most one in any or all of the three coordinates that a voxel may have. This is equivalent to saying they share a face, edge, or corner. For any blob or grouping in the section scan, the voxel having the highest amplitude is determined and compared to the highest amplitude of other groupings, if present, and the location of the largest amplitude in the section saved in memory. This largest amplitude is considered to be the "peak" amplitude value for that section being processed. Since the geometric position of each peak is known in each section, the depth of each peak from outer surface 31 of the rib leg 23 may be calculated 72. Once all section scans have been processed to determine the location of the peak value for each section, a median value of the depth of all peak amplitudes value is calculated 73 and saved as single value under variable name "medianDepth."

Next, each scan is processed again to determine the "main peak" in each scan section 74. This is done by determining the location for the "main peak" and "tip peak" for each section. The main peak location is found by finding all contiguous blobs of amplitude above the configurable minimum used in step 72 above (i.e. the variable mainPeakMinAmplitude). For each blob the process calculates the absolute value of the difference between the blob's peak's depth (variable="blobPeakDepth") from the median depth variable medianDepth. This distance is assigned the variable name "distanceToMedianDepth" which is a "distance" value only in the depth dimension from surface 31. If this value is greater than some configurable maximum (i.e. variable called "mainPeakMaxDistFromMedianDepth"). Then that blob is removed from further consideration.

Once all such blobs are gathered, if no blobs exist in the section scan then that scan section is flagged as "Review Recommended" under a report listing (see FIG. 7) and the next scan section is processed. If blobs exist in the scan section, the blobs are processed using the following sub-processing description:

Assign variables blob1 and blob2 with peak amplitudes as amplitude1 and amplitude2 (respectively) and define a score (blob1, blob2) as follows:

1. Let depthScore1=distanceToMedianDepth1+0.2
2. Let depthScore2=distanceToMedianDepth2+0.2
3. Let depthScore=ln(depthScore1/depthScore2) (with ln=natural logarithm)
4. Let amplitudeScore=ln(amplitude2/amplitude1)
5. Let depthAmplitudeFactor be a configurable value from 0.0 and 1.0 (with a default value assigned as 0.30)
6. Let score=((1.0−depthAmplitudeFactor)*depthScore)+(depthAmplitudeFactor*amplitudeScore)

A representative pseudo code to implement the above process may be found in Table 1.0 below:

TABLE 1.0

Determine the "main peak" using (blob1, blob2)

1. Let X be the first blob
2. For each other blob Y:
   1. Let A = score(X, Y)
   2. Let B = score(Y, X)
   3. If B < A then set X = Y
3. At the end of this process, the main peak is X Therefore, a final score between each blob equals a weighted average of depthScore and amplitudeScore using depthAmplitudeFactor as the weighting factor. Using this procedure, the blob that has the smallest score when compared to any other blob constitutes the "main peak" within the particular section scan being processed.

Next, we consider all blobs other than the "main" peak above some minimum amplitude (tipPeakMinAmplitude) in an attempt to find the "tip" peak per the sub-process below. If there are no such blobs, then there is no "tip" peak value and the search subprocess below is skipped. The minimum amplitude for variable tipPeakMinAmplitude is established in the same manner as the mainPeakMinAmplitude above by calculating a range distribution of all amplitudes and only searching for relevant amplitudes above a percentage of the highest values in order to exclude noise and other non-relevant scanning artifacts. The "tip" peak is found by defining a search area of voxels (i.e. a "rectangular" subset of voxels whose coordinates lie between a minimum and maximum beam angle and a minimum and maximum sound path as defined below) and looking for blobs (other than the "main" blob) whose peaks intersect this search area as follows:

Define the "tip" peak search area around the "main" peak as follows: a search area in which all voxels satisfy the following criteria:

1. The voxel beam angle is ≥the main peak beam angle
2. The voxel beam angle is <the main peak beam angle plus 12°
3. The voxel sound path is ≤the main peak sound path
4. The voxel sound path is >the main peak sound path minus 0.050" (¹⁄₂₀th of an inch)

While known in the PAUT system industry, for clarity, the above terms are defined below for convenience:

Voxel Beam Angle means the angle from the probe transceiver 42 on which the particular voxel lies. Typically, these angles range between 45 and 70 degrees and are separated by 1-degree increments.

Voxel Sound Path means the range or distance of the voxel under scrutiny from the probe transceiver 42.

Main Peak Beam Angle means in polar coordinates for any voxel the angle of the main peak blob. Since any blob will have a plurality of voxels, the "main peak beam angle is the angle in the polar coordinates for the voxel having the highest amplitude, or if there is more than one highest amplitude voxel in the blob the voxel closest to the center of the corresponding region of these highest amplitude voxels.

Main Peak Sound Path means in polar coordinates for any voxel the range or distance from the probe transceiver 42 of the main peak blob. Since any blob will have a plurality of voxels, the "main peak sound path is the range magnitude in the polar coordinates for the voxel having the highest amplitude, or if there is more than one highest amplitude voxel in the blob the voxel closest to the center of the corresponding region of these highest amplitude voxels.

We then identify all candidate tip peak blobs whose peak is within this search area. If there are zero, there is no "tip" peak. If only a single tip peak blob is found, it is selected as the "tip" peak. If more than one tip peak blobs are found, the tip peak with the smallest value (i.e. shallowest depth relative to the leg outer surface 31) is selected as the "tip" peak.

Once the above variables and values have been found and saved in memory, a lack of penetration or "LOP" may be found 76 for each section scan and stored and reported for a particular weld seam testing. As is known, LOP is counterintuitively calculated as the actual percentage that a weld extends into the joint to be welded relative to the thickness of the rib leg thickness.

The LOP may be found 76 using the procedure described below. The procedure uses the tip peak location found per the procedure described above, but if no tip peak location was found a substitute value is used. The substitute value is defined by the following:

Find the point further along the same main beam path where the amplitude has dropped off from its main peak maximum by −6 dB (this is also known as a "6 db drop" which is essentially a 50% drop in magnitude). That location will be selected as the substitute value for the tip peak location.

The LOP value 76 may be calculated with the following steps:
1. Let depthDifference be the absolute value of the difference in depth of the main and tip peaks.
2. Let penetration=1.0−depthDifference
3. If this value is out of bounds (e.g. <70% or >100%) then flag the scan position as being out of spec. This numerical range (x≤70% or x≥100%) may be altered by defining a different numerical range filter 78 depending upon bridge engineer specifications for the weld seam. Table 2.0 below shows pseudo code for calculating whether the penetration value is out of bounds and includes references to the values shown in example report 90 shown in FIG. 7.

TABLE 2.0

Penetration Value Acceptance

Let K = thickness of part
Let MPD = median peak depth (will be some fraction of the full thickness K)
Let M = depth of main peak
Let T = depth of tip peak
Let D = |M − T| [column P 99 on Report 90]
Let P_input = 1.0 − (D / K) [column Q on Report 90]
Let P_median = 1.0 − (D / MPD) [column R 102 on Report 90]
Accept if P_input ≥ 70% and P_input ≤ 100% [column S 104 on Report 90]

Weld seam statistics may also be calculated after each LOP is calculated per the above and selectively displayed 64, such as the following statistics:
1. The average of penetration over all scans for a weld seam;
2. What fraction of scans for the difference between the main peak depth and the median depth is above 0.090".

The seam statistics may also be used to produce a pass/fail calculation based on the number/density/etc. of out-of-spec scan sections.

Referring to FIG. 7, a report may be generated giving scanning values recorded and calculated using the above described processes. Example report 90 shows an example scan acquired using an OmniScan Mx2 32/128 PAUT instrument collecting data with an Olympus 10L32-A10 probe having an SA10-N55S wedge, with scanning movement controlled with an Olympus WeldROVER scanner and data taken every 0.02 inches. The probe included 32 trigger elements with the beam thickness set at approximately 80% of the thickness of the rib leg 23, which in this case was 0.385 inches thick. The thickness of the steel deck plate 14 was approximately 1 inch, with all steel tested being mild carbon steel. Scanning resolution granularity was set at 0.25 of a degree instead of a nominal 1-degree resolution.

Column A 91 shows an assigned scan section number (numerically discontinuous in part because only selected portions of a scan are reproduced in this example report) that references different scan positions D 93 (here in inches) along the weld seam. The main beam angle E 96 is the angle of the beam at which the main blob was found in the noted section scan, along with a main blob amplitude value F 97 as a percentage of full screen height of the PAUT instrument. Height P 99 represents the gap g distance in inches in the weld 22. Value Q 101 is the percentage penetration 28 by the weld 22 and R 102 is the median value of the percentage penetrations for the entire measured weld seam. Column S 104 provides a pass (accept-green), or fail (reject-red), or review (yellow) color coding to allow rapid visual indicators for a weld examiner to determine the individual and grouped 111 performance of individual welds and the recorded weld seam. Evaluator (e.g. a weld inspector) notes field T 106 are also provided so that prepopulated text may be inserted into a generated report or so that an operator may insert their own notes or replace the prepopulated notes. An inspection summary tab may also be selectable 112 so that overall statistics of the weld seam may be provided as described above. As may be understood, certain sections of the weld seam may need to be recommended for review 109 so that a weld inspector may visually inspect that section of the weld seam or do a manual PA ultrasonic test of that section to determine if the section requires remediation. As may be understood, the hope is that most or an acceptable portion of the weld seam has satisfactory levels of weld penetration (e.g. 111), such as 70%-80%, or other selectable range predetermined for each weld seam data file analysis. However, as will be understood, bridge engineers establish the weld design specifications to meet bridge design loading requirements and an acceptable range will vary from bridge to bridge. In the disclosed example, 70% to 100% weld penetration was specified by engineers as acceptable, with any penetration greater than 100% being defined as a melt through.

While I have shown my invention in one form, it will be obvious to those skilled in the art that it is not so limited but is susceptible of various changes and modifications without departing from the spirit thereof.

Having set forth the nature of the invention, what is claimed is:

1. In an orthotropic steel decking bridge assembly having a deck plate and a leg of a rib supporting said deck plate, a testing procedure for determining a penetration amount of a weld seam joining said leg to said deck plate comprising the steps of:
  a. scanning a portion of said weld seam using an ultrasonic tester, wherein said scanning step produces a scan data file comprising a plurality of sectional scans along said weld seam;
  b. saving said scan data file in computer memory storage;
  c. using a computer processor to access said scan data file and in each said sectional scan finding at least one contiguous set of voxels having a magnitude greater than a predetermined minimum;
  d. locating the highest magnitude voxel in each said contiguous set of voxels;
  e. for each sectional scan, calculating the depth of each said highest magnitude voxel in said weld; and,
  f. calculating a penetration depth percentage for each section scan based upon the thickness of said leg metal by comparing said depth of said highest magnitude voxel to said thickness of said leg metal and saving said penetration percentage in computer memory storage.

2. The method of claim 1, further including the step of calculating a median depth value for all depths of each said highest magnitude voxel in said each said weld sectional scans.

3. The method of claim 2, further including the step of producing a human discernable report that indicates whether each sectional scan meets a predetermined penetration value for each said weld.

4. The method of claim 3, wherein said step of producing a human discernable report includes the step of producing a color-coded portion indicating a color assignment as a status indicator for each sectional scan.

5. The method of claim 2, further including the step of based on said calculated median depth value calculating a median penetration value for the entire weld seam and determining whether said median penetration value meets a predetermined acceptance value for said weld seam in accordance with bridge design specifications.

6. The method of claim 1, further including the steps of:
  a. for each section scan, find the number of contiguous sets of voxels present; and,
  b. for all section scans that include more than one contiguous sets of voxels, calculate a weighted average of a magnitude score and a depth score using a predetermined depth magnitude factor for each said contiguous sets of voxels to arrive at said penetration depth.

7. The method of claim 6, further including the step applying a numerical range filter to said set of penetration values for each sectional scan and calculating which sectional scans meet said range filter requirements.

8. The method of claim 7, wherein said range filter comprises a pass or fail status.

9. The method of claim 6, further including the step of looking for a tip peak and based on the location of said tip peak enhancing the location of said main peak.

10. The method of claim 1, further including the step of in any sectional scan if only a single set of contiguous sets of voxels is present in said sectional scan then apply a 6 db drop to the magnitude of said contiguous set of voxels and recalculate the penetration value for said sectional scan.

11. In an orthotropic steel decking bridge assembly having a deck plate and a leg of a rib supporting said deck plate, a testing procedure for determining a penetration amount of a weld seam joining said leg to said deck plate comprising the steps of:
  a. step for scanning a portion of said weld seam using an ultrasonic tester, wherein said scanning step produces a scan data file comprising a plurality of sectional scans along said weld seam;
  b. step for saving said scan data file in computer memory storage;
  c. using a computer processor to access said scan data file step for in each said sectional scan finding at least one contiguous set of voxels having a magnitude greater than a predetermined minimum;
  d. step for locating the highest magnitude voxel in each said contiguous set of voxels;
  e. for each sectional scan, step for calculating the depth of each said highest magnitude voxel in said weld; and,
  f. step for calculating a penetration depth percentage for each section scan based upon the thickness of said leg metal by comparing said depth of said highest magnitude voxel to said thickness of said leg metal and saving said penetration percentage in computer memory storage.

12. The method of claim 11, further including the steps of:
  a. for each section scan, find the number of contiguous sets of voxels present; and,
  b. for all section scans that include more than one contiguous sets of voxels, calculate a weighted average of a magnitude score and a depth score using a predetermined depth magnitude factor for each said contiguous sets of voxels to arrive at said penetration depth.

13. The method of claim 12, further including the step of calculating a median depth value for all depths of each said highest magnitude voxel in said each said weld sectional scans.

14. The method of claim 13, further including the step of in any sectional scan if only a single set of contiguous sets of voxels is present in said sectional scan then apply a 6 db drop to the magnitude of said contiguous set of voxels and recalculate the penetration value for said sectional scan.

15. The method of claim 14, further including the step applying a numerical range filter to said set of penetration values for each sectional scan and calculating which sectional scans meet said range filter requirements.

16. The method of claim 15, wherein said range filter comprises a pass or fail status.

17. The method of claim 16, further including the step of producing a human discernable report that indicates whether each sectional scan meets a predetermined penetration value for each said weld.

18. The method of claim 17, wherein said step of producing a human discernable report includes the step of producing a color-coded portion indicating a color assignment as a status indicator for each sectional scan.

19. The method of claim 18, further including the step of based on said calculated median depth value calculating a median penetration value for the entire weld seam and determining whether said median penetration value meets a predetermined acceptance value for said weld seam in accordance with bridge design specifications.

20. In an orthotropic steel decking bridge assembly having a deck plate and a leg of a rib supporting said deck plate, a method of determining a lack of penetration at a selected location in a weld seam joining said leg to said deck plate from an ultrasonic scan data file including a plurality of sectional scans of said weld seam comprising the steps of:
  a. using a computer processor to access said scan data file and in each said sectional scans finding at least one contiguous set of voxels having a magnitude greater than a predetermined minimum;

b. locating the highest magnitude voxel in each said contiguous set of voxels;
c. for each sectional scan, calculating the depth of each said highest magnitude voxel in said weld;
d. calculating a lack of penetration value for each section scan based upon the thickness of said leg metal by comparing said depth of said highest magnitude voxel to said thickness of said leg metal and saving said lack of penetration values as a set representative of said weld seam in computer memory storage; and,
e. based on said saved set of penetration values, producing a human discernable report indicating a median lack of penetration value for said weld seam.

* * * * *